US009861656B2

(12) United States Patent
Nicolson et al.

(10) Patent No.: US 9,861,656 B2
(45) Date of Patent: *Jan. 9, 2018

(54) PHOSPHOLIPID COMPOSITIONS AND USE THEREOF TO ENHANCE SPERMATOZOA MOTILITY AND VIABILITY

(71) Applicant: ALLERGY RESEARCH GROUP, LLC, Alameda, CA (US)

(72) Inventors: Garth Nicolson, Huntington Beach, CA (US); Gonzalo Ferreira de Mattos, Montevideo (UY); Robert A. Settineri, Irvine, CA (US)

(73) Assignee: ALLERGY RESEARCH GROUP, LLC, Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/256,245

(22) Filed: Sep. 2, 2016

(65) Prior Publication Data

US 2016/0367590 A1    Dec. 22, 2016

Related U.S. Application Data

(63) Continuation-in-part of application No. 14/815,841, filed on Jul. 31, 2015, now Pat. No. 9,468,668, which is a continuation-in-part of application No. 14/152,938, filed on Jan. 10, 2014, now Pat. No. 9,095,507, which is a continuation-in-part of application No. 13/208,255, filed on Aug. 11, 2011, now Pat. No. 8,877,239.

(60) Provisional application No. 62/245,868, filed on Oct. 23, 2015, provisional application No. 62/216,269, filed on Sep. 9, 2015.

(51) Int. Cl.
*A61K 31/733* (2006.01)
*A61K 31/685* (2006.01)
*A61K 31/661* (2006.01)
*A61K 31/683* (2006.01)
*A61K 31/70* (2006.01)
*C12N 5/076* (2010.01)

(52) U.S. Cl.
CPC .......... *A61K 31/733* (2013.01); *A61K 31/661* (2013.01); *A61K 31/683* (2013.01); *A61K 31/685* (2013.01); *A61K 31/70* (2013.01); *C12N 5/061* (2013.01); *C12N 2500/05* (2013.01); *C12N 2500/32* (2013.01); *C12N 2500/34* (2013.01); *C12N 2500/38* (2013.01); *C12N 2501/90* (2013.01); *C12N 2501/999* (2013.01)

(58) Field of Classification Search
CPC ............ A23V 2250/5062; A61K 31/66; A61K 31/683; A61K 31/70; A23D 9/013; Y10S 514/96; Y10S 514/962
See application file for complete search history.

(56) References Cited

U.S. PATENT DOCUMENTS

| 5,989,583 A | * | 11/1999 | Amselem ............... A61K 9/145 424/439 |
| 2006/0257490 A1 | * | 11/2006 | Cremer ..................... A23J 7/00 424/489 |
| 2006/0275506 A1 | * | 12/2006 | Fisher ...................... A23L 2/52 424/641 |

OTHER PUBLICATIONS

Niness (Journal of Nutrition, Jul. 1999, vol. 129, pp. 1402S-1406s).*
Raetz (Annual Review of Genetics, 1986, vol. 20, pp. 253-295).*

* cited by examiner

*Primary Examiner* — Mark V Stevens
(74) *Attorney, Agent, or Firm* — Koppel, Patrick, Heybl & Philpott (57) ABSTRACT

Sperm mobility and impregnation of an oocyte is enhanced by placing sperm in an aqueous solution of phospholipids prior to in vitro fertilization or artificial insemination. The aqueous phospholipid solution can also be used during storage or cryopreservation of the sperm. Also, the motility of sperm produced or ejaculated and the environment into which it is placed is enhanced my ingestion of the phospholipid composition by the male or female, or a vaginal placement of compositions containing the phospholipids.

16 Claims, 9 Drawing Sheets

| SPERM VELOCITY CHARACTERISTICS | | | | | |
|---|---|---|---|---|---|
| | | | PROGRESSIVE | MEDIUM PROGRESSIVE | FAST PROGRESSIVE |
| MEAN AMPLITUDE OF LATERAL HEAD DISPLACEMENT | ALH ($\mu$M) | CONTROL | 2.2 | 1.4 | 2.3 |
| | | 1%NTFL | 10.1 | 5.3 | 10.6 |
| BEAT CROSS FREQUENCY | BCF (Hz) | CONTROL | 2.5 | 1.7 | 2.9 |
| | | 1%NTFL | 10.5 | 7.2 | 13.6 |

FIG. 5

| MEAN SPERM HEAD SIZE | | | | | | |
|---|---|---|---|---|---|---|
| | | TOTAL | STATIC | SLOW | MEDIUM | FAST |
| SPERM HEAD AREA ($\mu^2$) | CONTROL | 16.2 | 16.8 | 16.9 | 14.6 | 14.1 |
| | 1%NTFL | 18.8 | 19.2 | 19.2 | 18.8 | 18.2 |

FIG. 6 fig. 7 fig. 8 fig. 9A fig. 9B

| SPERM VELOCITY CHARACTERISTICS (CENTRIFUGED) | | | | | |
|---|---|---|---|---|---|
| | | | PROGRESSIVE | MEDIUM PROGRESSIVE | FAST PROGRESSIVE |
| MEAN AMPLITUDE OF LATERAL HEAD DISPLACEMENT | ALH (μM) | CONTROL | 2.2 | 1.4 | 2.3 |
| | | 0.1%NTFL | 2.35 | 1.5 | 2.6 |
| BEAT CROSS FREQUENCY | BCF (Hz) | CONTROL | 10.2 | 5.3 | 10.6 |
| | | 0.1%NTFL | 10.2 | 6.9 | 12.7 | fig. 10

PHOSPHOLIPID COMPOSITIONS AND USE THEREOF TO ENHANCE SPERMATOZOA MOTILITY AND VIABILITY

CROSS REFERENCE TO RELATED APPLICATIONS

This application claims benefit of U.S. Provisional Application 62/245,868 filed Oct. 23, 2015 and U.S. Provisional Application 62/216,269 filed Sep. 9, 2015, both entitled PHOSPHOLIPID COMPOSITIONS AND USE THEREOF TO ENHANCE SPERMATOZOA MOTILITY AND VIABILITY. The present application is also a CIP of U.S. patent application Ser. No. 14/815,841 filed Jul. 31, 2015, which is a CIP of U.S. patent application Ser. No. 14/152,938 filed Jan. 10, 2014, now U.S. Pat. No. 9,095,507 (the '507 patent) issued Aug. 4, 2015, which is a CIP of U.S. patent application Ser. No. 13/208,255 filed Aug. 11, 2011, now U.S. Pat. No. 8,877,239 (the '239 patent) issued Nov. 4, 2014, are hereby incorporated herein in their entirety by reference, including the drawings, charts, schematics, diagrams and related written description.

BACKGROUND

Field of the Invention

The present invention relates to methods for maintaining or enhancing sperm motility, counteracting the effects of aging and exposure to environmental factors that can reduce sperm motility, and providing a more friendly environment in the womb or in vitro and in turn increase the likelihood of fertilization of oocytes through vaginal or in vitro insemination. It also relates to preservation of mammalian sperm for human and animal insemination, for example in livestock breeding.

Description of the Related Art

Sperm motility is a crucial factor for successful fertilization of oocytes (i.e., conception). The composition of the plasma membrane of the sperm is one the factors influencing sperm motility. The effects of aging, exposure to oxidative entities and changes in membrane lipid composition are important factors affecting male fertility. It has also been shown that changes in sperm membrane lipid composition are important factors resulting in a reduction in motility and the likelihood of fertilization. Peroxidation of the membrane lipids is also an important factor affecting for sperm health in adult life and as an individual ages.

The sperm cell has a unique structure and function. The sperm cell is viable in a body different from its origin, namely a female body, and is capable of navigating through the vagina and uterus to fertilize an egg released from the ovaries. The plasma membrane of the sperm cell also has a lipid composition different from most other cell membranes. It contains high amounts of polyunsaturated fatty acids (PUFA), particularly diPUFA (phospholipids esterified with two PUFA). PUFA are known to contribute to membrane fluidity and flexibility. The specific membrane lipid composition of the sperm cell has been found to be important for specific sperm functions promoting the creation of microdomains with different fluidity, fusogenicity, and permeability characteristics required for the sperm to navigate to, and to penetrate and fuse with the oocyte.

Phospholipids are key constituents of the lipid fraction of the sperm cell membranes, with phosphatidylcholine, phosphatidylethanolamine, and sphingomyelin being the major components. The lipid and fatty acid composition of sperm cells differ for different animals and different species as well as for fertile and subfertile population of the same species. Therefore, published data on non-human sperm viability may not be translatable to the performance or viability of human sperm.

It is known that cryopreservation can affect the sperm membrane of non-human sperm. Further, freezing and thawing results in lipid modifications and domains of the sperm head plasma membrane react differently to cryopreservation. Furthermore, some studies investigated the ability of sperm cells in boar and bull semen to take up lipid components or fatty acids from the surrounding environment during incubation in vitro.

(Vasquez and Roldan, 1997) and, furthermore, Buhr et al. (1999) suggested a link between successful cryopreservation of boar semen and a given mixture of lipids and fatty acids in the original diluent. Once again, a specific role for the lipids present in the diluent or exchanges with spermatozoa are indicated. The present data also indicate that there was not only an uptake of lipid by sperm cells but also that this uptake was related to the quality of fresh semen. Phospholipase activities may mediate this lipid metabolism, totally or in part (for review, see Roldan, 1998). Buhr et al. (1994) reported an increase in the content of phospholipids, and in particular of phosphatidylcholine, during the cryopreservation of boar spermatozoa in the presence of egg yolk. The exact role of yolk components has not yet been clarified. Phosphatidylcholine (also called lecithin) has been proposed as the protective component during freezing (Quinn et al., 1980) since it prevented ultrastructural damage and favoured the maintenance of motility and respiration (Simpson et al., 1987). In contrast, studies have shown that phosphatidylcholine had no effect on boar sperm damage (Purse) et al., 1973) and did not prevent motility loss during cold shock and storage at −58 C (Watson, 1981). Phosphatidylserine has also been proposed as a protective agent in the boar (Butler and Roberts, 1975; Foulkes, 1977). Cationic low density lipoprotein (LDL) of egg yolk, characterized by a specific lipid:protein ratio of 2.7, was found to be the most efficient in protecting bull spermatozoa against cold shock. The cationic protein moiety of the LDL complex bound strongly to the sperm plasma membrane, which is negatively charged, and the lipid moiety was responsible for the protective action." (Vishwanath et al., 1992). "Changes In Sperm Quality And Lipid Composition During Cryopreservation Of Boar Semen" S Cerolini, A Maldjian, F Pizzi, T M Gliozzi—*Reproduction*, 2001—Soc Reprod Fertility.

The major problem associated with cryopreservation of sperm cells is the loss of viability as a result of the freezing and thawing process. Loss of viability is related to membrane leakiness which is induced by sperm phospholipids peroxidation.

Infertility issues impact approximately 15% of all couples trying-to-conceive. Male infertility is a contributing factor in about half of these cases and high concentrations of oxidative-stress-causing agents have been identified in 30-80% of infertile men. Studies on the delivery of vitamin supplements and amino acids show an enhancement of specific sperm parameters (count, morphology, motility). Some antioxidants such as these vitamin C, selenium, vitamin E, L carnitine, Vitamin A, zinc and grapeseed extract have been shown to promote healthy sperm count, sperm morphology, and sperm motility, while reducing oxidative damage from agents, free radicals, or biological interactions that causes oxidative stress. (Dawson E B et al. Effects of ascorbic acid on male fertility. Ann N Y Acad Sci 1987; 498: 312-23).

SUMMARY

NT Factor Lipids (NTFL) are compositions containing inulin and purified membrane glycerolphospholipids, as set forth in U.S. Pat. No. 8,877,239 (the '239 patent) and U.S.

Pat. No. 9,095,507 (the '507 patent) and U.S. application Ser. No. 14/815,841, all incorporated herein in their entirety by reference, are powerful nutrients for antioxidant therapy and cell membrane repair. The '239 patent describes the formulation and delivery of those phospholipids composition for maintaining or restoring cell and mitochondrial health in the human body, or a specific organ system within the human body, or treating a specific disease or phospholipid deficiency within human body, said composition comprising a mixture of phospholipids or phospholipid precursors including a suitable carrier medium, and particularly in the form of a tablet, capsule or powder. The '507 patent and Ser. No. 14/815,841 describe and claim delivery of the NTFL compositions in the form of a chewable wafer or tablet. However, those patents do not show or suggest that the phospholipid compositions, referred to herein as NTFL or NT Factor Lipids, when ingested by a male will enhance the environment within the reproductive organs or semen of the male so as to result in improved vitality and motility of sperm cells produce by that male. Those patents also do not show or suggest that the phospholipid compositions, when ingested by a female will enhance the environment within the female sexual organs or cervical mucus and as a result provide an improved environment to receive the sperm and enhance the sperm motility to increase the likelihood of conception. Nor do those patents show or suggest that the NTFL phospholipids in solution will provide a more suitable fertilization environment and enhanced sperm motility when used in cryopreservation, during in vitro fertilization or prior to or during normal sexual activity intended to result in oocyte fertilization.

Set forth herein are the results of incubation of mature spermatozoa from healthy human donors with solutions containing NTFL phospholipids. It has been found by applicants that exposure of spermatozoa to the NTFL phospholipids reduces and/or reverses damage to the exposed spermatozoa and increases sperm motility, particularly in the most mobile sperm, and the resultant increased likelihood of egg fertilization. While data on preservation of animal sperm may not be directly translatable to human, it has been found that human data appears to be relevant to preservation of sperm from livestock used in artificial insemination in animal breeding and similar benefits have been found.

DETAILED DESCRIPTION

NTFL is a phospholipid composition described in U.S. patent application Ser. No. 13/208,255, issued as U.S. Pat. No. 8,887,259 incorporated in its entirety herein by reference. Said phospholipid composition comprises inulin and a mixture of phospholipids comprising phosphatidylglycerol and one or more phospholipids selected from the group consisting of phosphatidylcholine (PC), phosphatidylethanolamine (PE), phosphatidylinositol (PI), and phosphatidylserine (PS), and one or more of linoleic acid (LA) and phosphatidic acid. In a preferred embodiment NTFL phospholipid components comprises 19-29% phosphatidylcholine (PC), 15-25% phosphatidylethanolamine (PE), 3.5%-10% phosphatidic acid (PA), 10-18% phosphatidylinositol (PI), 2-10% phosphatidylglycerol (PG), 10-20% glycolipids, and 5-11% other phospholipids. This composition along with inulin was used in the studies herein. In another preferred composition mixture of phospholipids having about 25% to about 29% phosphatidylglycerol (PG), about 68% to about 72% phosphatidylcholine (PC), and up to about 5% phosphatidylethanolamine (PE), and may optionally include about 1% to about 5% phosphatidylinositol (PI) and phosphatidylserine (PS).

Based on data collected regarding the ability of aqueous solutions of NTFL compositions containing phospholipid to enhance sperm motility in vitro and the ability of ingested NTFL phospholipid compositions to improve mitochondrial heath and function throughout the body, enhanced sperm motility can be provided by delivering the NTFL composition to a male individual to create an enhanced phospholipid environment in said individual's semen or to a female to create an enhanced phospholipid environment in said female individual's vaginal fluids or cervical mucus. The NTFL composition can be delivered in the form of a tablet, capsule or powder as set forth in U.S. Pat. No. 8,877,239. In one embodiment the powdered NTFL may be incorporated in a food product or blended into a suitable liquid and consumed in the form of a beverage, which may be cold or heated. In the alternative, the NTFL powder may be formed into an edible wafer or tablet, for example by compaction in a tablet press such as described in U.S. patent application Ser. No. 14/815,841 and U.S. Pat. No. 9,095,507 referred to above, or divisional or CIP applications thereof. In a still further embodiment the phospholipid mixture may be included in a vaginal suppository or vaginal lubricant, cream, jelly, foam or gel delivered prior to or directly after sexual intercourse, such as described below. Further, NTFL compositions containing phospholipids are also beneficial additives in solutions for collecting, storing and preserving (including cryopreservation) live spermatozoa from humans and animals for artificial insemination and in vitro fertilization. Addition of one or more antioxidants such as these vitamin C, selenium, vitamin E, L carnitine, Vitamin A, zinc and grapeseed extract to the NTFL phospholipid compositions are also beneficial in further enhancing the increase in sperm motility demonstrated by the use of NTFL.

Described below is an evaluation of the beneficial effect of NTFL phospholipid compositions on the motility of sperm. Increased sperm motility, all other factors remaining constant, will increase the likelihood of an oocyte being penetrated by the sperm, whether in vivo or in vitro, which in turn results in an enhanced likelihood of egg fertilization.
Comparative Tests.

Healthy human male participants aged 20 to 51 with no known infertility conditions donated sperm samples (n=12). Using the swim-up method the samples were treated to obtain viable spermatozoa. Multiple comparable portions of the viable spermatazoa were then collected for the comparative evaluations described below.

Sperm samples were placed in control solutions of HamF10 (see Table 1) and HamF10 containing NTFL at different concentrations (0.1 to 3% g/ml) and incubated for periods of 1 to 4 hours in an incubator containing a 5% $CO_2$ atmosphere were compared. The NTFL glycerolphospholipids, were found to be incorporated into the spermatozoa membranes in incubations of at least about two hours based on the correlation between sperm head area and NTFL %. After the incubation, the samples were centrifuged at low velocity (approximately 500-1000 RPM in a 10 cm centrifuge, preferably 800 RPM) and later observed in a Leja Chamber for examination with Computer Assisted Sperm Analysis (CASA) (Hirano Y, Shibahara H, Obara H, Suzuki T, Takamizawa S, et al. "Andrology: Relationships Between Sperm Motility Characteristics Assessed By The Computer-Aided Sperm Analysis (CASA) And Fertilization Rates In Vitro". J Assist Reprod Genet (2001); 18: 215-220). An average of 10 treatments at 37° C. were evaluated (SCA, Microptics). Other samples were treated at lower temperatures (24° C. or 30° C.), to test the effect of NTFL under stress conditions such as temperature. The same procedure was also performed with samples incubated at 37° C. with $H_2O_2$ as a chemical oxidative stress agent.

TABLE 1

| Ham's F10* | | | |
|---|---|---|---|
| Component | mg/lt | Mol. Wt. | Mol. (mM) |
| Amino Acids | | | |
| L-Alanine | 89.10000 | 89.1 | 1.00 |
| L-Arginine HCl | 2107.00000 | 174.2 | 12.10 |
| L-Asparagine H2O | 150.10000 | 150.1 | 1.00 |

TABLE 1-continued

| Ham's F10* | | | |
|---|---|---|---|
| Component | mg/lt | Mol. Wt. | Mol. (mM) |
| L-Aspartic Acid | 133.10000 | 133.1 | 1.00 |
| L-Cysteine HCl H2O | 351.30000 | 175.6 | 2.00 |
| L-Glutamic Acid | 147.10000 | 147.1 | 1.00 |
| Glycine | 75.10000 | 75.07 | 1.00 |
| L-Histidine HCl H$_2$O | 209.60000 | 209.6 | 1.00 |
| L-Isoleucine | 26.20000 | 131.2 | 0.20 |
| L-Leucine | 131.20000 | 131.2 | 1.00 |
| L-Lysine HCl | 293.00000 | 182.6 | 1.60 |
| L-Methionine | 44.80000 | 149.2 | 0.30 |
| L-Phenylalanine | 49.60000 | 165.2 | 0.30 |
| L-Proline | 115.10000 | 115.1 | 1.00 |
| L-Serine | 105.10000 | 105.1 | 1.00 |
| L-Threonine | 35.70000 | 119.1 | 0.30 |
| L-Tryptophan | 6.10000 | 204.2 | 0.03 |
| L-Tyrosine | 18.10000 | 181.2 | 0.10 |
| L-Valine | 35.10000 | 117.1 | 0.30 |
| Vitamins | | | |
| Biotin | 0.24000 | 244.3 | 0.0010 |
| Choline Chloride | 6.98000 | 139.6 | 0.05 |
| D-Calcium Pantothenate | 7.15000 | 238.3 | 0.03 |
| Folic Acid | 13.20000 | 441.4 | 0.03 |
| myo-Inositol | 5.41000 | 180.2 | 0.03 |
| Nicotinamide | 6.11000 | 122.13 | 0.05 |
| Pyridoxine HCl | 2.06000 | 205.6 | 0.01 |
| Riboflavin | 3.76000 | 376.4 | 0.01 |
| Thiamine HCl | 10.12000 | 337.3 | 0.03 |
| Vitamin B12 | 13.60000 | 1355.4 | 0.01 |
| Inorganic Salts | | | |
| Calcium Chloride Dihydrate [CaCl2 2H2O] | 441.00000 | 147.0 | 3.00 |
| Cupric Sulfate [CuSO4] | 0.01600 | 159.68 | 0.0001 |
| Ferrous Sulfate Heptahydrate [FeSO4 7H2O] | 8.34 | 278.0 | 0.03 |
| Magnesium Sulfate [MgSO4] | 746.00000 | 120.4 | 6.20 |
| Potassium Chloride [KCl] | 2850.00000 | 74.55 | 38.23 |
| Potassium Phosphate Monobasic [KH2PO4] | 830.00000 | 136.09 | 6.10 |
| Sodium Chloride [NaCl] | 74000.00000 | 58.44 | 1266.26 |
| Sodium Phosphate Dibasic [Na2HPO4] | 1562.00000 | 141.96 | 11.00 |
| Zinc Sulfate Heptahydrate [ZnSO4 7H2O] | 0.28800 | 287.5 | 0.0010 |
| Other | | | |
| Dextrose | 11000.00000 | 180.2 | 61.04 |
| Hypoxanthine | 40.80000 | 136.1 | 0.30 |
| Lipoic Acid | 2.06000 | 206.3 | 0.01 |
| Phenol Red Sodium Salt | 12.40000 | 376.4 | 0.03 |
| Sodium Pyruvate | 1100.00000 | 110.0 | 10.00 |
| Thymidine | 7.27000 | 242.2 | |

*Ham, R. G., Exptl. Cell Res., v. 39, 515 (1963).

Figure 1:
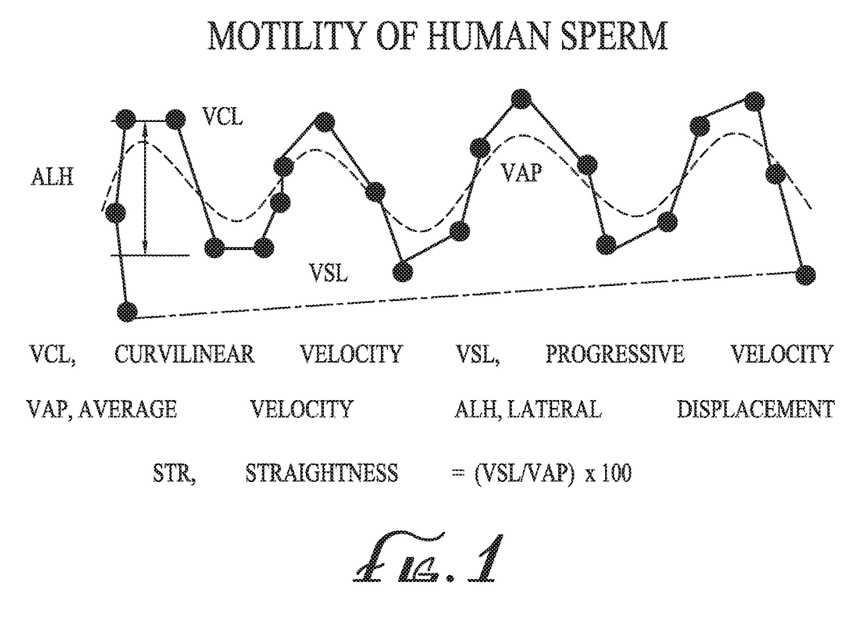
FIG. 1 illustrates the elements of sperm motility.

FIG. 1 illustrates the elements of sperm motility where:
VCL—Curvilinear velocity—Velocity of sperm in a trajectory for progression
VSL—Progressive velocity—Velocity of sperm in an axis straight line for progression
VAP—Average velocity—Velocity measured on a mean sperm trajectory for progression. All velocities are measured in µM/s)
LIN—Linearity—Ratio of axis straight line and curved trajectory velocities (VSL/VCL)
STR—Straightness—Ratio of straight line and mean trajectory velocities (VSL/VAP)
WOB—Oscillation index—Oscillation of trajectory about an spatial average path. These indexes are expressed as %

ALH—Amplitude of the lateral displacement of the head from mean axis straight line (μM)

BCF—Beat Cross Frequency—Number of times per second that sperm crosses the Mean axis straight line (Hz)

FIG. 1 shows the characteristics of motility and velocity of human sperm (usually measured in micrometer/sec). The solid line curve (VCL) represents the actual curvilinear velocity or track of a single motile sperm cell, whereas the dashed line curve represents the average velocity (VAP) of many sperm cells. The movement consists of the amplitude of lateral movement or displacement (ALH) of the sperm head from a straight line and progressive (forward or straight-line) movement (VSL). The straightness velocity of movement (STR) can be defined as VSL/VAPX100. The figure illustrates all the motility parameters shown in the WHO manual on sperm studies to be relevant to fertility.

Figure 2:
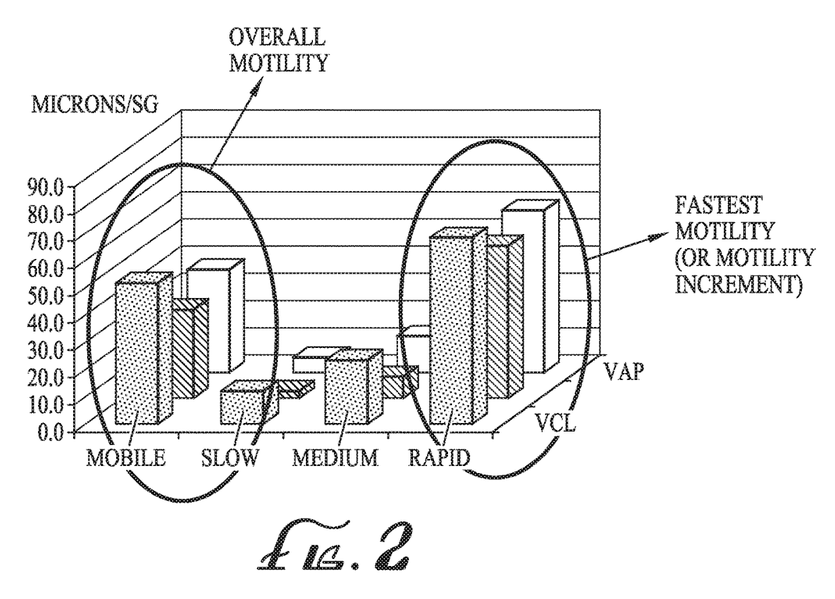
FIG. 2 is a graphical representation of the motility of human sperm.

FIG. 2 is a graphical representation showing the distribution of sperm motility in a typical collected sample (identified as mobile) with the sample broken down into three classifications, namely, slow, medium and rapid and, within each classification the curvilinear and average velocity.

The differences between those motilities, are explained in the WHO Laboratory Manual For Examination And Processing Of Human Semen (5th Edition), World Health Organization, (2010). According to the Manual, when discussing sperm motility, it is important to specify total motility (PR+NP) or progressive motility (PR). A simple system for grading motility is recommended that distinguishes spermatozoa with progressive or non-progressive motility from those that are immotile. The motility of each spermatozoon is graded as follows:

a. Progressive motility (PR): spermatozoa moving actively, either linearly or in a large circle, regardless of speed;

b. Non-progressive motility (NP): all other patterns of motility with an absence of progression, e.g. swimming in small circles, the flagellar force hardly displacing the head, or when only a flagellar beat can be observed; and c. Immotility (IM): no movement.

The previous edition of this manual recommended that progressively motile spermatozoa should be categorized as rapid or slow, with a speed of >25_m/sec at 37° C. defining "grade a" spermatozoa. However, it is difficult for technicians to define the forward progression so accurately without bias (Cooper &Yeung, 2006).

FIG. 2 shows a typical experiment and the data that results from analysis of the various parameters of sperm motility showing an average motility (all motile or mobile sperm) and the sperm motility separated into several velocity categories specifically slow, medium and rapidly moving motile sperm.

Figure 3A:
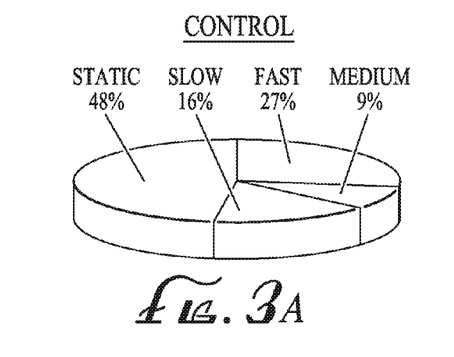
FIGS. 3A and 3B comprise two pie charts comparing the sperm velocity characteristics of a control sperm sample to the same sperm sample after exposure for 3 hours to a 1% NTFL concentration.
Figure 3B:
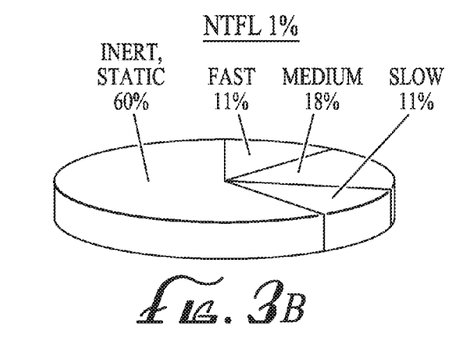

The pie charts in FIG. 3 show progressive motility as fast, medium and slow and non-progressive motility, immotile spermatozoa percentage (static). Slow progressive motility is represented by slow or medium mobile sperm. FIGS. 3A and 3B show the distribution of sperm activity for a control sperm sample (FIG. 3A) compared to the same sperm sample after exposure for 3 hrs to a 1% NTFL concentration (FIG. 3B). The data shows significant improvements in sperm motility but this can only be seen at lower NTFL concentrations where the NTFL micelles don't interfere with sperm motility as a result of impact of NTFL micelles with sperm. For example, in concentrations between 0.01 and 0.3%, particularly from 0.1-0.3%, sonicated, micro-emulsified NTFL samples sperm motility was increased. This was also found in sperm samples at the higher NTFL concentrations (1%) where the sperm were separated from the NTFL micelles by brief centrifugation. In other words, sperm motility was actually significantly increased in the sample with 1% NTFL, but the increase could not be properly measured due to the sperm collision with NTFL micelles.

Figure 4A:
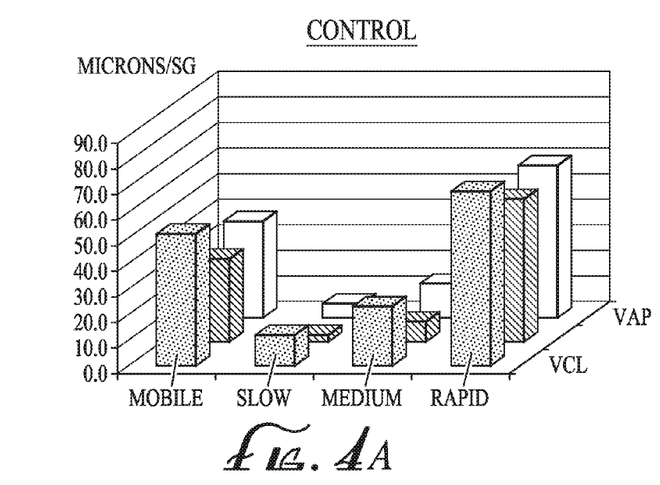
FIGS. 4A and 4B comprise two 3 axis bar charts comparing control sperm samples to 1% NTFL treated sperm.
Figure 4B:
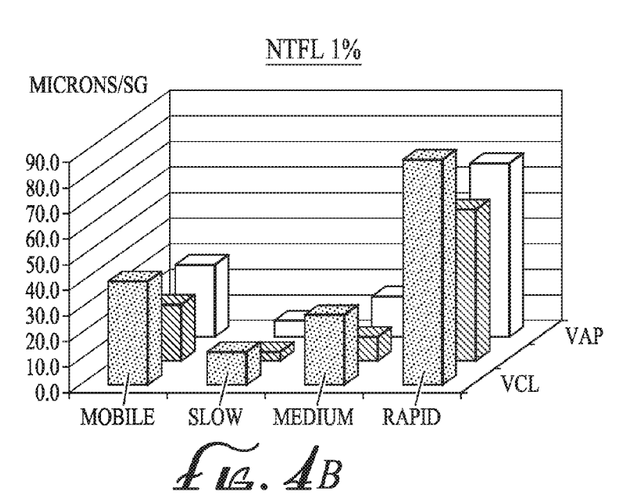

FIGS. 4A and 4B are 3 axis bar charts comparing the same control sperm samples to 1% NTFL treated sperm as in FIGS. 3A and 3B. At NTFL concentrations near 1% the overall velocities of sperm in the sample were reduced due to micelle collisions and motility interference. The bars in the right row of the chart illustrate mobile, rapidly moving sperm involved in collisions with relatively large lipid micelles. Motile sperm, however, had an average increase in velocities (VCL, VSL, VAP, LIN, STR, WOB) of 18±4% ($p<0.05$ independent t-test).

Figure 5:
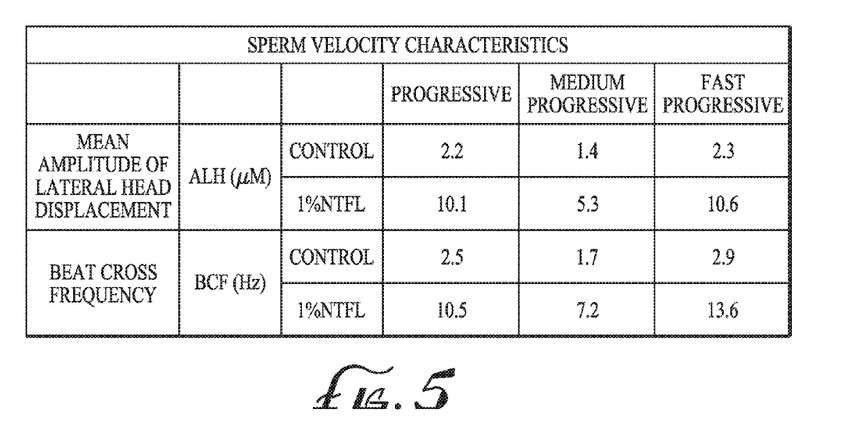
FIG. 5 is a table comparing the mean amplitude of lateral head displacement and the beat cross frequency of sperm in both the control and following incubation in the 1% NTFL solution.

FIG. 5 is a table comparing the mean amplitude of lateral head displacement (ALH) and the beat cross frequency (BCF) of sperm in both the control and following incubation in the 1% NTFL solution. The presence of NTFL phospholipids increases ALH and BCF which are critical for fertility prediction in a sperm sample. These parameters related to flagella activity, especially BCF, which are indicative of the strength of penetration during fertility, were also increased by approximately the same amount and at the same significance level.

Figure 6:
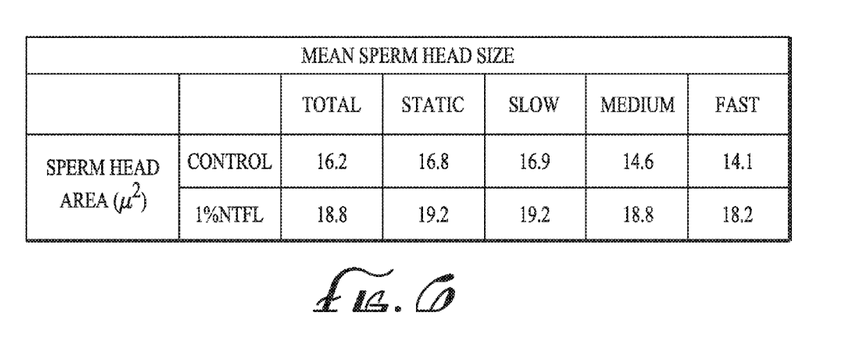
FIG. 6 is a table comparing the sperm head area ($\mu^2$) in both the control and following incubation in the 1% NTFL solution.

To test if the NTFL composition becomes incorporated into the sperm membrane, changes in the sperm head area were determined. FIG. 6 is a table comparing the sperm head area ($\mu^2$) in both the control and following incubation in the 1% NTFL phospholipid solution. A statistically significant increase in sperm head velocity was found to occur in all NTFL incubated sperm cells in the sample, indicating a significant incorporation of the NTFL into each sperm cell. Alternatively, it was found that a comparison of a 123 Rhodamine stained control sperm sample with a stained sperm sample in a NTFL 0.02% solution, even when exposed to 300 uM of $H_2O_2$, showed a significant increase in cytoplasmic droplets in spermatozoa in a confocal field of sperm seeded at the same concentration (an increase from 12% to 72%, $p<0.05$). 123 Rhodamine stains mostly mitochondrial membranes and plasma membrane regions in the midpiece, neck and subequatorial head of the sperm cell. Xu, Yuan et al. (2013) has pointed that the presence of cytoplasmic droplets is indicative of healthy and motile sperm (Hui Xu, Shui-Qiao Yuan, Zhi-Hong Zheng, and Wei Yan, "The Cytoplasmic Droplet May Be Indicative Of Sperm Motility And Normal Spermiogenesis", *Asian J Androl.* (2013 November); 15(6): 799-805).

Figure 7:
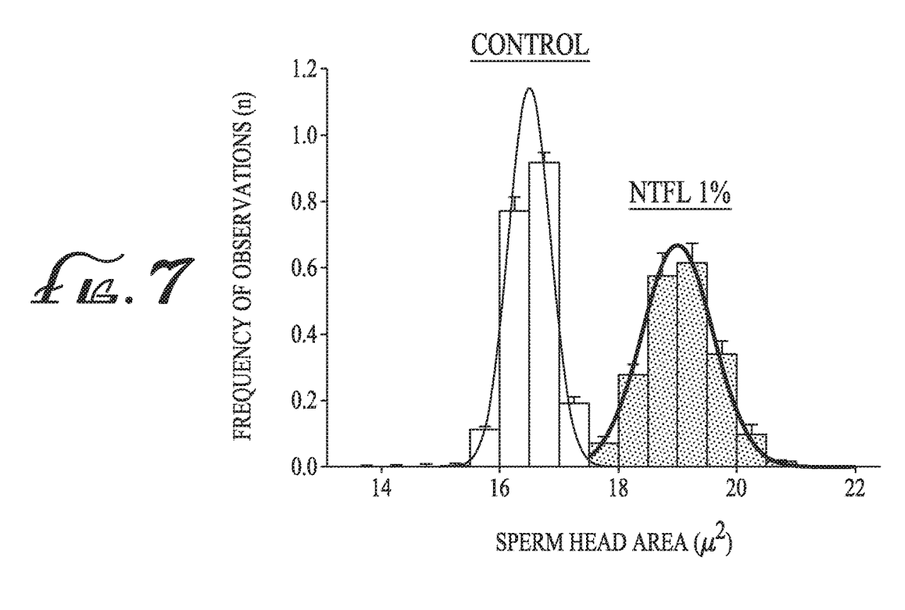
FIG. 7 is a graph comparing the normal distribution of sperm head size in the Control with the 1% NTFL incubated sample.

FIG. 7 is a graph comparing the normal distribution of sperm head size in control solutions with equivalent sperm samples incubated in a 1% NTFL solutions. The significant increase in sperm head area from an average of 16 μm in the Control to 19 μm in the NTFL solution ($p<0.05$, independent t-test) and a greater distribution thereof shows that NTFL incorporates into the sperm head.

Figure 8:
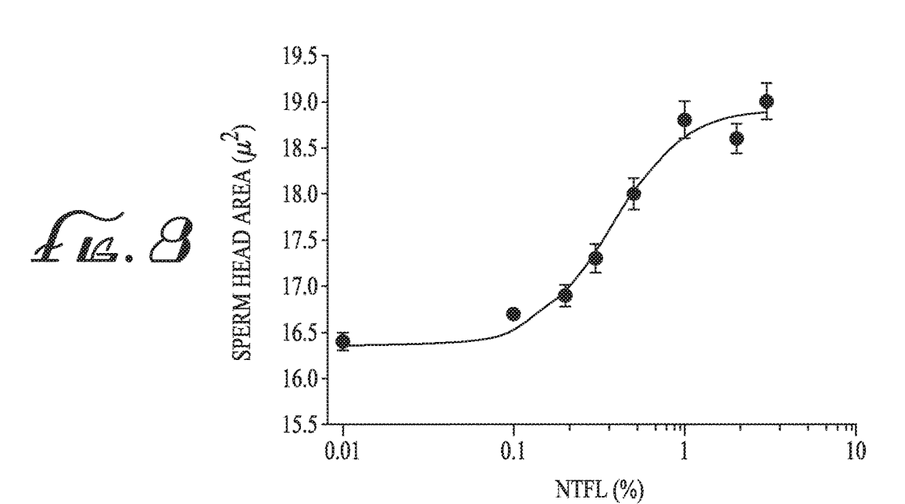
FIG. 8 is a semi-log graph illustrating the increase in sperm head area as a function of NTFL for concentrations up to about 2%.

FIG. 8 is a graph (semi-log) illustrating the increase in sperm head area as a function of NTFL solution concentrations for concentrations up to about 2% in the solution showing that sperm head area increases as the concentration increases.

Figure 9A:
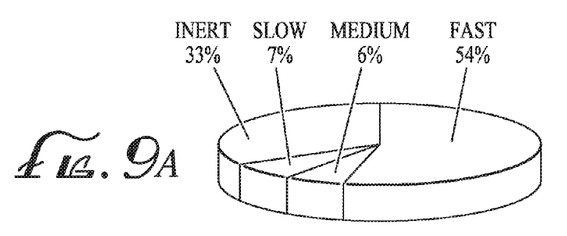
FIG. 9A is a pie cart and FIG. 9B is a bar chart illustrating the effect of a 0.1 NTFL solution on a centrifuged sample of sperm.
Figure 9B:
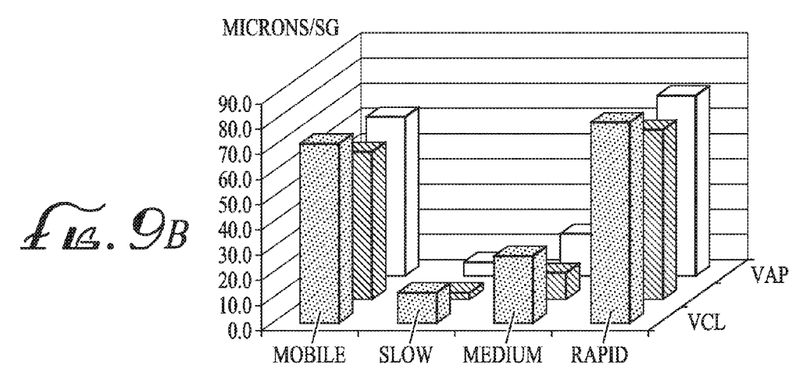

FIG. 9A is a pie chart and FIG. 9B is a 3 dimensional bar chart illustrating the effect of a 0.1 NTFL solution on a centrifuged sample of sperm. Recognizing that NTFL incorporates into the sperm head, the interference resulting from the presence of micelles was reduced by preparing centrifuged sperm samples to separate the sperm from the lipid micelles. At lower NTFL concentrations the velocities of all sperm were found to be increased. Separation of the sperm cells from the lipid micelles by low speed centrifugation made the enhanced motility of sperm cells by the presence of even a small amount of NTFL more obvious. In addition, sonication and micro-emulsification of NTFL, showed significantly improvement at NTFL concentrations between 0.01 to 0.3%.

Figure 10:
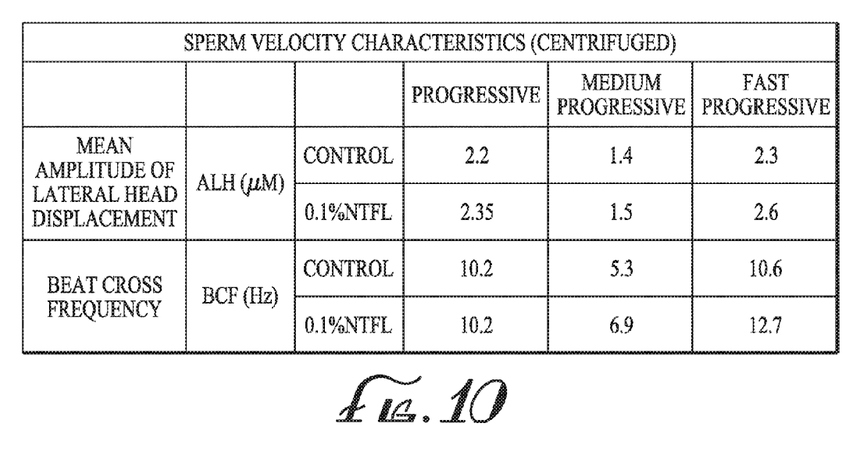
FIG. 10 is a table illustrating sperm velocity characteristics of centrifuged sperm samples after exposure to the 0.1% NTFL.

FIG. 10 is a Table illustrating the sperm velocity characteristics of the centrifuged sperm samples after exposure to the 0.1% NTFL. While centrifuging enhanced the characteristics of the Control sample, ALH and BCF are still increased by exposure to 0.1% NTFL centrifuged sperm samples, showing its usefulness at these concentrations to promote hyperactivated states (increase of BCF), which is associated with better fertility and healthier sperm. This effect is even more pronounced in the fastest spermatozoa, meaning that the presence of NTFL improves all sperm but is even more effective on the fastest spermatozoa which are the best sperm for causing egg fertilization.

Figure 11A:
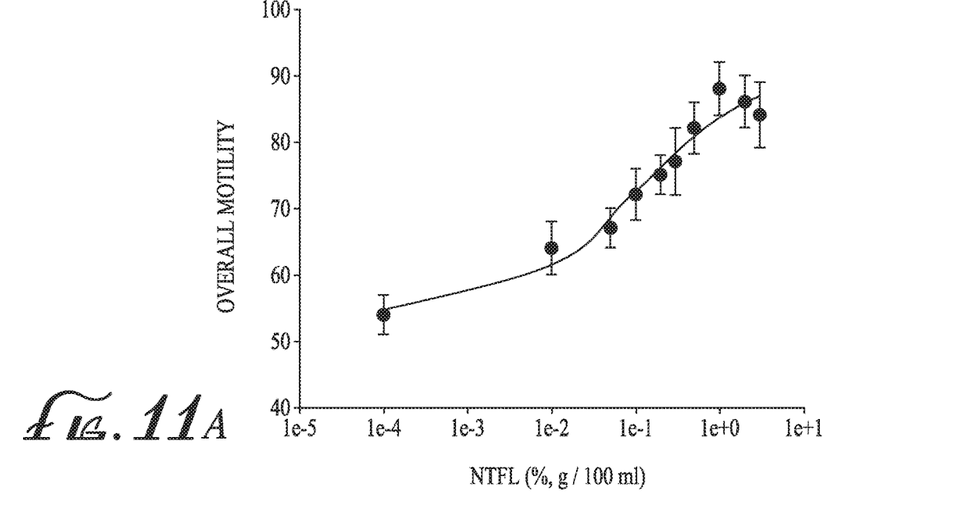
FIGS. 11A and 11B are graphs showing dose response curves for overall motility and motility of the fastest sperm cells.
Figure 11B:
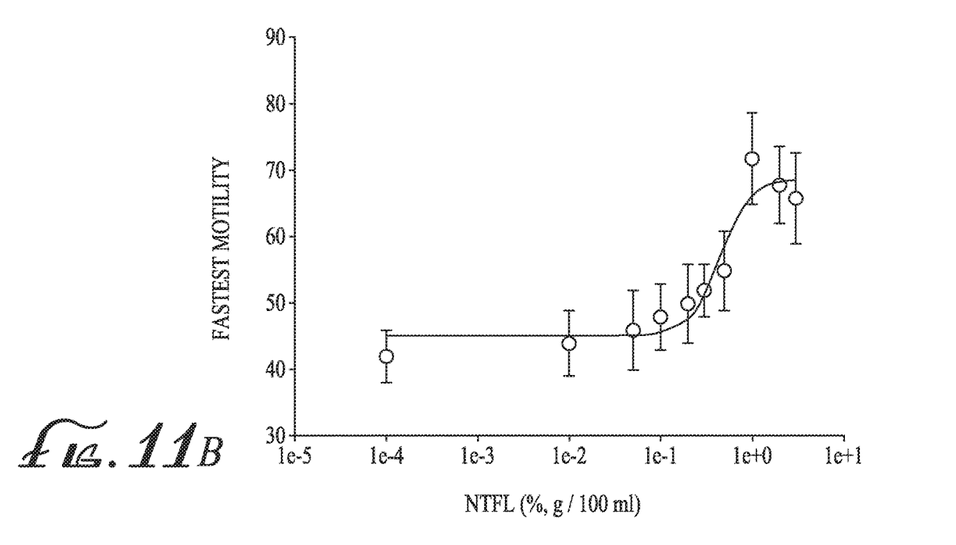
Figure 12A:
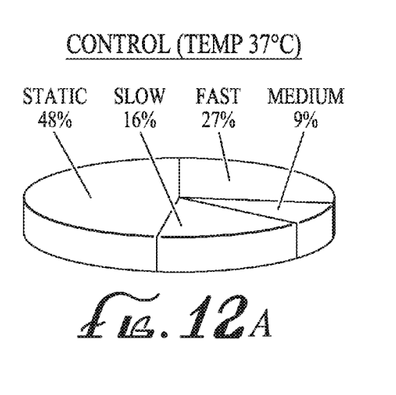
FIGS. 12A and 12B are pie charts illustrating the effect of low temperature on sperm motility.
Figure 12B:
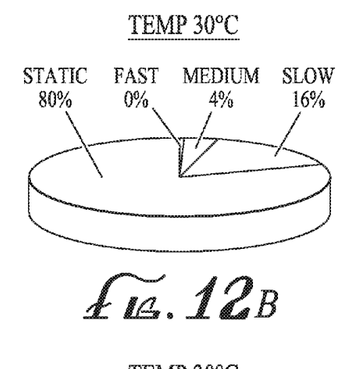
Figure 12C:
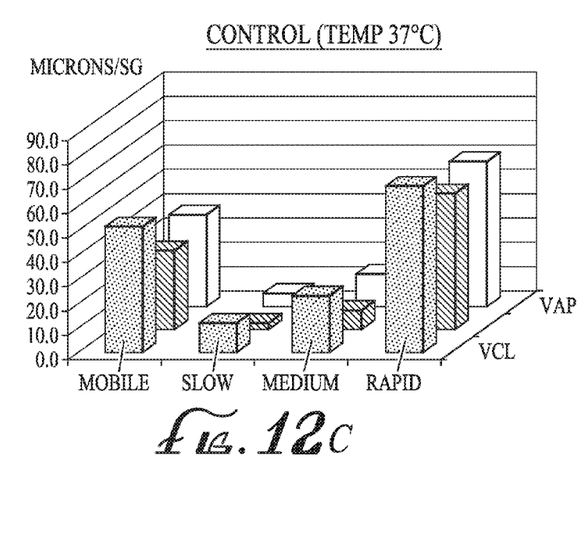
FIGS. 12C and 12D are 3-dimensional bar charts also illustrating the effect of low temperature on sperm motility.
Figure 12D:
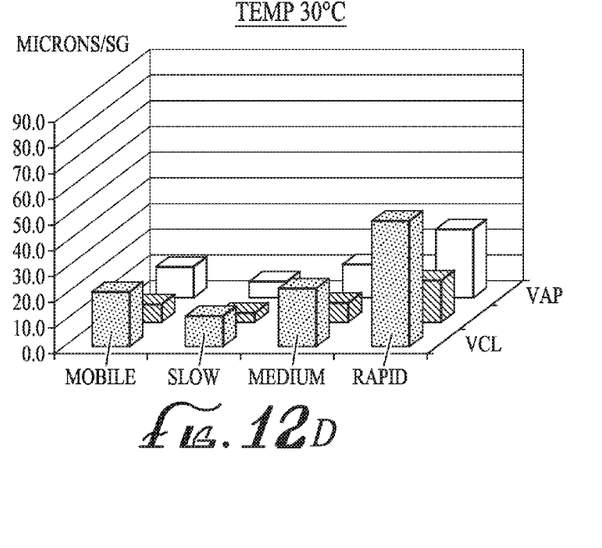

FIGS. 11A and 11B show dose response curves for overall motility and motility of the fastest sperm cells. Both velocities are increased upon centrifugation. However, at concentrations approaching 1% there is a tendency for a reduction in motility because of micelle interference and the head is probably too heavy for the flagella to properly function. The effect is more pronounced and has an IC50 of approximately 0.5% for the fastest sperm compared with overall motile sperm. When cells were separated from the lipid micelles by low speed centrifugation, the enhanced motility of sperm cells was more obvious for overall and fastest motility, with increasing NTFL concentration.

Figure 13A:
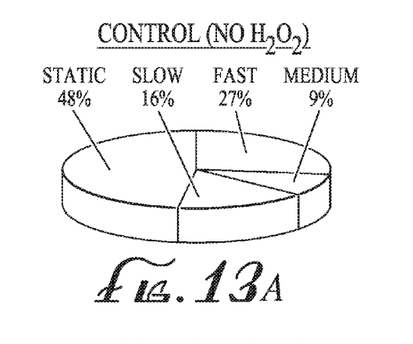
FIGS. 13A and 13B are pie charts illustrating the effect of oxidation on sperm motility.
Figure 13B:
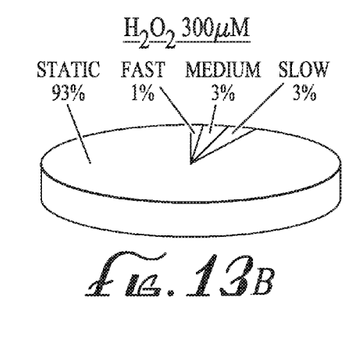
Figure 13C:
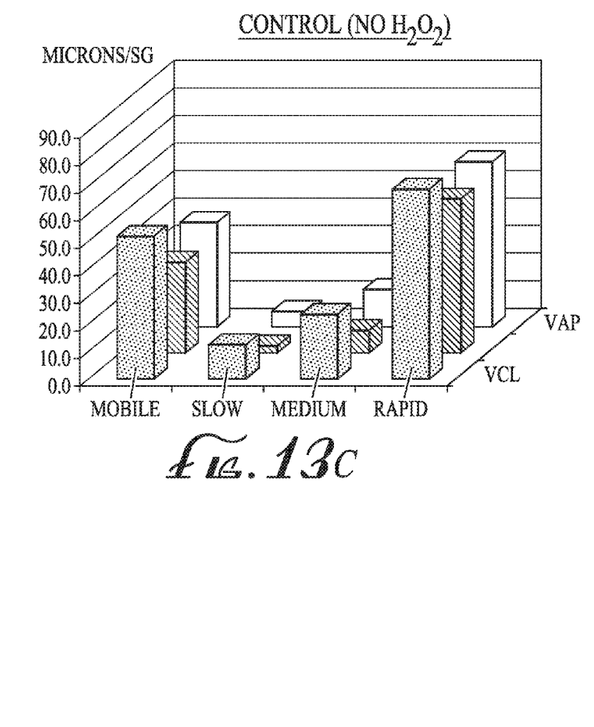
FIGS. 13C and 13D are 3-dimensional bar charts also illustrating the effect of oxidation on sperm motility.
Figure 13D:
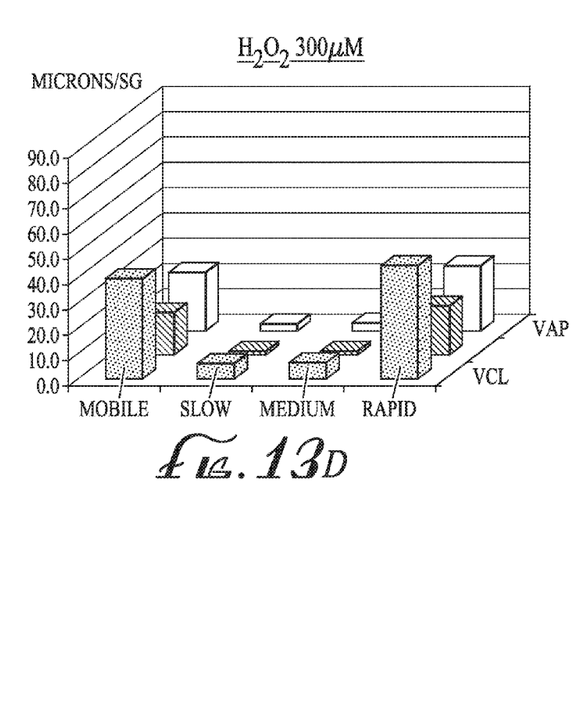
Figure 14A:
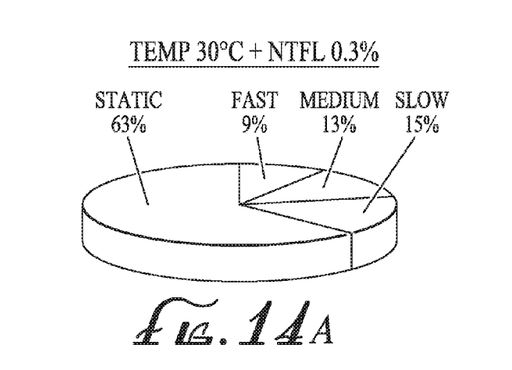
FIG. 14A is a pie chart illustrating that 0.3% NTFL ameliorates the reduction of motility caused by exposure to low temperature.
Figure 14B:
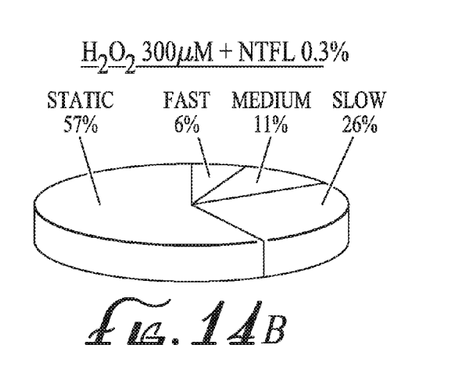
FIG. 14B is a pie chart illustrating that 0.3% NTFL also ameliorates the reduction of motility caused by exposure to oxidation.
Figure 14C:
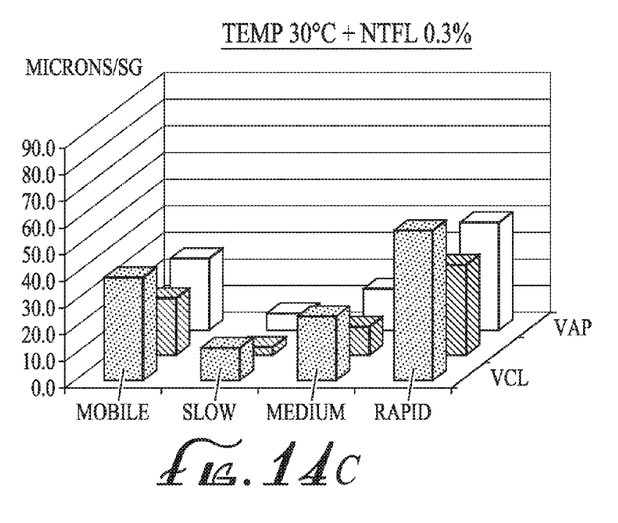
FIG. 14C is a 3-dimensional bar chart also illustrating that exposure to 0.3% NTFL ameliorates the reduction of motility caused by exposure to low temperature.
Figure 14D:
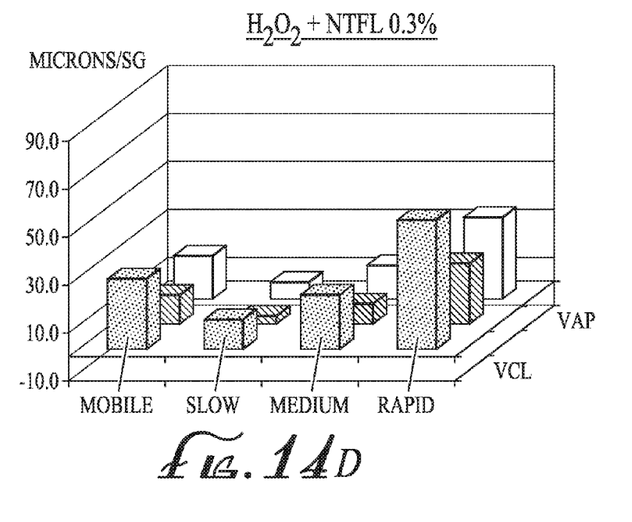
FIG. 14D is a 3-dimensional bar chart also illustrating that exposure to 0.3% NTFL ameliorates the reduction of motility caused by exposure to $H_2O_2$.

FIGS. 12A, 12B, 12C, 12D, 13A, 13B, 13C and 13D illustrate the effect of low temperature or oxidation respectively on sperm motility. Increasing oxidative stress with hydrogen peroxide or stress by physical means, such as lowering temperatures, decreases sperm motility, and thus all sperm velocities were reduced (FIGS. 13a and 13B). Also, the fraction of static or non-mobile spermatozoa was increased.

FIGS. 14A, 14B, 14C and 14D show that exposure to 0.3% NTFL ameliorates the reduction of motility caused by exposure to lower temperatures or exposure to $H_2O_2$, illustrating that NTFL is also an effective agent to protect spermatozoa against oxidative damage, which is one of the primary causes of male infertility.

Based on the data set forth in the Figures and discussed above it is concluded that the motility and capacity of active sperm in the semen obtained from healthy donors is improved by exposure to NTFL. Although the benefits of using concentrations of NTFL near 1% are not readily seen without centrifugation to remove large NTFL micelles that result in collisions with sperm, exposure of sperm to NTFL concentrations below 1% were shown to be real and reproducible. Motile sperm exposed to NTFL had an average increase in sperm velocity parameters (VCL, VSL, VAP, LIN, STR, WOB) of 18.4%. Sperm motility parameters related to flagella activity, which is an indication of the ability to penetrate ovum during fertilization, were also increased by approximately the same degree (ALH and BCF)

Confirming that the NTFL was incorporated into sperm membranes was shown by the increase in sperm head size (increase in sperm head membrane area) during incubation with NTFL. The average size of the sperm heads increased with NTFL concentrations, from an average of 16 um to 19 um. When sperm cells were separated from the lipid micelles by low speed (about 500-1000 RPM) centrifugation, the enhanced motility of the sperm cells was more obvious in the overall sperm population.

Dose-response curves for overall motility effects showed an IC50 of approx. 0.5%, with motility increments with exposure to 0.1%-0.3% NTFL. Even under stress produced by low temperature or oxidation (hydrogen peroxide) exposures, swim-up results obtained for sperm exposed to a 0.1% NTFL solution maintained overall motility and the velocities and flagella assessment showed increases of about 20% for the highly motile sperm which comprises the sperm population primarily responsible for fertilization.

Human sperm exposed to, or stored in a solution containing an NTFL composition is effective in protecting sperm functionality against damage by physical or oxidative stress. The NTFL composition is a specific combination of inulin with membrane glycerolphospholipids selected to maintain or enhance the normal sperm cell membrane phospholipid composition. A preferred NTFL composition comprises inulin and a mixture of phospholipids comprising phosphatidylglycerol and one or more phospholipids selected from the group consisting of phosphatidylcholine (PC), phosphatidylethanolamine (PE), phosphatidylinositol (PI), and phosphatidylserine (PS), and one or more of linoleic acid (LA) and phosphatidic acid. In a more preferred embodiment NTFL phospholipid components comprises 19-29% phosphatidylcholine (PC), 15-25% phosphatidylethanolamine (PE), 3.5%-10% phosphatidic acid (PA), 10-18% phosphatidylinositol (PI), 2-10% phosphatidylglycerol (PG), 10-20% glycolipids, and 5-11% other phospholipids. Alternatively, a preferred composition mixture of phospholipids has about 25% to about 29% phosphatidylglycerol (PG), about 68% to about 72% phosphatidylcholine (PC), and up to about 5% phosphatidylethanolamine (PE), and may alternatively include optionally further comprising about 1% to about 5% phosphatidylinositol (PI) and phosphatidylserine (PS).

Accordingly, since it has been shown that ingestion of NTFL compositions including glycerolphospholipids results in the dissemination and incorporation of the glycerolphospholipids into cellular membranes throughout the body, ingestion of NTFL compositions including phospholipids by a male are expected to result in the incorporation of NTFL phospholipids into sperm cells and the environment where sperm are produced and stored in the body resulting in greater sperm motility in semen.

Further, based thereon it is concluded that exposure of sperm to NTFL compositions including the phospholipids during sperm development and production (spermatogenesis), storage or maturation in males will increase the quality and motility of sperm, and in particular, the quality and motility of the most active and motile fraction of sperm that are most likely to be involved in fertilization. Thus even when the male is considered to be infertile due to lowered sperm motility, or has impaired sperm motility as a result of aging, oxidative stress, variations in ambient temperature or adverse physical conditions, such as elevated inflammation or other conditions, NTFL compositions including pholipids are expected to increase the quality and enhance the motility of ejaculated sperm.

Administering NTFL compositions including phospholipids to a male over a period of time is expected to result in an improvement in the quality of sperm produced by that individual. Administering NTFL compositions including phospholipids to a female over a period of time will likewise enhance the environment in which the sperm is placed and also increase fecundity of the female, thus increasing the likelihood of conception. Thus, the use of NTFL compositions by both males and females further enhance fertility and the likelihood of successful fertilization. It appears that these results can also be applied to livestock reproduction particularly in bovines by artificial means.

It is further concluded that ingestion, or other forms of delivery of the NTFL composition to a female, for example, using an NTFL containing suppository, by placement of a solution of NTFL within the vagina prior to intercourse or artificial insemination will create an environment for enhanced motility of the sperm subsequently introduced into the vagina.

For example, a fertility enhancing vaginally deliverable NTFL composition can be formed by replacing the nonoxynol-9, or other spermicidal additives with NTFL in vaginal spermicidal creams, jellies, foams, gels, and suppositories or adding NTFL to vaginal lubricants.

Administering NTFL to a male over a period of time will result in an improvement in the quality of sperm produced by that individual, administering NTFL to a female over a period of time will likewise enhance the environment in which the sperm is placed and may also increase fecundity of the female, thus increasing the likelihood of conception, and the use of NTFL compositions by both the male and female will further enhance the likelihood of the sperm fertilizing and oocyte.

We claim:

1. A method of increasing sperm motility comprising delivering to a sexual organ of a male mammal, a female mammal or both a male and female mammal a composition comprising an effective amount of inulin and a mixture of phospholipids, said inulin and phospholipids delivered in the form of a vaginal cream, jelly, foam, gel, lubricant, or a suppository.

2. The method of claim 1 wherein the mixture of phospholipids comprises phosphatidylglycerol and one or more phospholipids selected from the group consisting of phosphatidylcholine (PC), phosphatidylethanolamine (PE), phosphatidylinositol (PI), and phosphatidylserine (PS), and one or more of linoleic acid (LA) and phosphatidic acid.

3. A method of increasing sperm motility comprising delivering to a male mammal, a female mammal or both a male and female mammal a composition comprising an effective amount of inulin and a mixture of phospholipids, wherein the composition is delivered in the form of
a) a tablet, capsule or powder, said powder added to a food product, blended into a beverage or compressed into a chewable tablet or
b) provided as 0.1 to 4% of a vaginal cream, jelly, foam, gel, lubricant or a suppository, wherein the phospholipid mixture comprises 19-29% phosphatidylcholine (PC), 15-25% phosphatidylethanolamine (PE), 3.5-10% phosphatidic acid (PA), 10-18% phosphatidylinositol (PI), 2-10% phosphatidylglycerol (PG), 10-20% glycolipids and 5-11% other phospholipids.

4. A method of increasing the likelihood of fertilization of a female oocyte by a sperm cell comprising delivering to a sexual organ of a male mammal, a female mammal or both a male and female mammal a composition comprising an effective amount of inulin and a mixture of phospholipids, said inulin and phospholipids delivered in the form of a vaginal cream, jelly, foam, gel, lubricant, or a suppository.

5. The method of claim 4 wherein the mixture of phospholipids comprises phosphatidylglycerol and one or more phospholipids selected from the group consisting of phosphatidylcholine (PC), phosphatidylethanolamine (PE), phosphatidylinositol (PI), and phosphatidylserine (PS), and one or more of linoleic acid (LA) and phosphatidic acid.

6. A method of increasing the likelihood of fertilization of a female oocyte by a sperm cell comprising delivering to a male mammal, a female mammal or both a male and female mammal a composition comprising an effective amount of inulin and a mixture of phospholipids, wherein the composition is delivered in the form of
a) a tablet, capsule or powder, said powder added to a food product, blended into a beverage or compressed into a chewable tablet or
b) provided as 0.1 to 4% of a vaginal cream, jelly, foam, gel, lubricant or a suppository, wherein the phospholipid mixture comprises 19-29% phosphatidylcholine (PC), 15-25% phosphatidylethanolamine (PE), 3.5-10% phosphatidic acid (PA), 10-18% phosphatidylinositol (PI), 2-10% phosphatidylglycerol (PG), 10-20% glycolipids and 5-11% other phospholipids.

7. A method of increasing the motility of sperm comprising depositing the sperm in an aqueous solution, the aqueous solution having an effective amount of inulin and a mixture of phospholipids dissolved therein.

8. The method of claim 7 wherein the mixture of phospholipids comprises phosphatidylglycerol and one or more phospholipids selected from the group consisting of phosphatidylcholine (PC), phosphatidylethanolamine (PE), phosphatidylinositol (PI), and phosphatidylserine (PS), and one or more of linoleic acid (LA) and phosphatidic acid.

9. The method of claim 7 wherein the inulin and the mixture of phospholipids dissolved in the aqueous solution comprises 0.1 to 4% of the aqueous solution.

10. The method of claim 7 wherein the phospholipid mixture comprises: 19-29% phosphatidylcholine (PC), 15-25% phosphatidylethanolamine (PE), 3.5%-10% phosphatidic acid (PA), 10-18% phosphatidylinositol (PI), 2-10% phosphatidylglycerol (PG), 10-20% glycolipids and 5-11% other phospholipids.

11. A method of increasing the likelihood of fertilization of a female ovum in vitro by a sperm cell comprising placing the sperm cells and ovum in an aqueous composition comprising an effective amount of inulin and a mixture of phospholipids.

12. The method of claim 11 where in the mixture of phospholipids comprises phosphatidylglycerol and one or more phospholipids selected from the group consisting of phosphatidylcholine (PC), phosphatidylethanolamine (PE), phosphatidylinositol (PI), and phosphatidylserine (PS), and one or more of linoleic acid (LA) and phosphatidic acid.

13. The method of claim 11 wherein said inulin and phospholipids in the aqueous solution comprise 0.1 to 4% of the aqueous solution.

14. The method of claim 11 wherein the phospholipid mixture comprises:
19-29% phosphatidylcholine (PC),
15-25% phosphatidylethanolamine (PE),
3.5%-10% phosphatidic acid (PA),
10-18% phosphatidylinositol (PI),
2-10% phosphatidylglycerol (PG),
10-20% glycolipids and
5-11% other phospholipids.

15. The method of claim 1 where in combination of inulin and phospholipids comprises 0.1 to 4% of the vaginal cream, jelly, foam, gel, lubricant or a suppository.

16. The method of claim 4 where in combination of inulin and phospholipids comprises 0.1 to 4% of the vaginal cream, jelly, foam, gel, lubricant or a suppository.

* * * * *